US012605089B2

(12) United States Patent
Kawara et al.

(10) Patent No.: US 12,605,089 B2
(45) Date of Patent: Apr. 21, 2026

(54) BIOLOGICAL ACTIVITY DETECTION SENSOR

(71) Applicant: Murata Manufacturing Co., Ltd., Nagaokakyo (JP)

(72) Inventors: Naoki Kawara, Nagaokakyo (JP); Atsushi Naito, Nagaokakyo (JP); Yutaka Takamaru, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 489 days.

(21) Appl. No.: 18/156,527

(22) Filed: Jan. 19, 2023

(65) Prior Publication Data

US 2023/0165485 A1      Jun. 1, 2023

Related U.S. Application Data

(63) Continuation of application No. PCT/JP2021/027852, filed on Jul. 28, 2021.

(30) Foreign Application Priority Data

Jul. 30, 2020      (JP) ................................. 2020-129036

(51) Int. Cl.
*A61B 5/11* (2006.01)

(52) U.S. Cl.
CPC .................................. *A61B 5/1101* (2013.01)

(58) Field of Classification Search
CPC ... A61B 5/1101; A61B 5/1107; A61B 5/4082; A61B 5/681; A61B 5/6829; A61B 5/6831; A61B 5/7264; A61B 2562/0219; A61B 2562/06; A61B 2560/0406; A61B 2560/0425; A61B 2560/0443
See application file for complete search history.

(56) References Cited

U.S. PATENT DOCUMENTS

| | | | |
|---|---|---|---|
| 6,997,882 B1 | 2/2006 | Parker et al. | |
| 10,182,728 B2 * | 1/2019 | Gu ............................. | A61B 8/13 |
| 10,244,985 B1 * | 4/2019 | Sayani ................... | A61B 5/318 |
| 2007/0208233 A1 | 9/2007 | Kovacs | |
| 2009/0306485 A1 | 12/2009 | Bell | |
| 2013/0076424 A1 | 3/2013 | Mohammad et al. | |

(Continued)

FOREIGN PATENT DOCUMENTS

| | | |
|---|---|---|
| JP | 2002186598 A | 7/2002 |
| JP | 2009528909 A | 8/2009 |

(Continued)

OTHER PUBLICATIONS

International Search Report in PCT/JP2021/027852, mailed Oct. 19, 2021, 4 pages.

*Primary Examiner* — Devin B Henson

(74) *Attorney, Agent, or Firm* — ArentFox Schiff LLP

(57) ABSTRACT

A biological activity detection sensor is provided that includes a motion detection sensor that detects motion of a living body, a tremor sensor that detects a tremor of the living body, and a base member that can be mounted on the living body. The base member includes a first member that is deformable in accordance with a mounted state on the living body, and a second member that is less deformable than the first member. The tremor sensor is provided in the first member, and the motion detection sensor is provided in the second member.

20 Claims, 18 Drawing Sheets

10E

(56)          References Cited

U.S. PATENT DOCUMENTS

| | | | |
|---|---|---|---|
| 2015/0051470 A1* | 2/2015 | Bailey | G06F 3/015 |
| | | | 600/300 |
| 2015/0272500 A1 | 10/2015 | Kan-Tor et al. | |
| 2016/0054185 A1 | 2/2016 | Servati et al. | |
| 2016/0262687 A1 | 9/2016 | Vaidyanathan et al. | |
| 2017/0027513 A1 | 2/2017 | Mulpuru | |
| 2018/0008195 A1 | 1/2018 | Vaitaitis | |
| 2018/0055449 A1* | 3/2018 | Ko | A61B 5/318 |
| 2018/0059714 A1* | 3/2018 | Martin | G06F 1/1635 |
| 2018/0263501 A1* | 9/2018 | Shim | A61B 5/01 |
| 2021/0330547 A1* | 10/2021 | Moaddeb | A61N 1/0452 |

FOREIGN PATENT DOCUMENTS

| | | | |
|---|---|---|---|
| JP | 2016042387 A | 3/2016 | |
| JP | 2016202603 A | 12/2016 | |
| JP | 2017042387 A | 3/2017 | |
| JP | 2020103429 A | 7/2020 | |
| WO | 2018074449 A1 | 4/2018 | |
| WO | 2019230411 A1 | 12/2019 | |

* cited by examiner

10

20

31,912

911

10

20

31,912

911

FIG. 4A
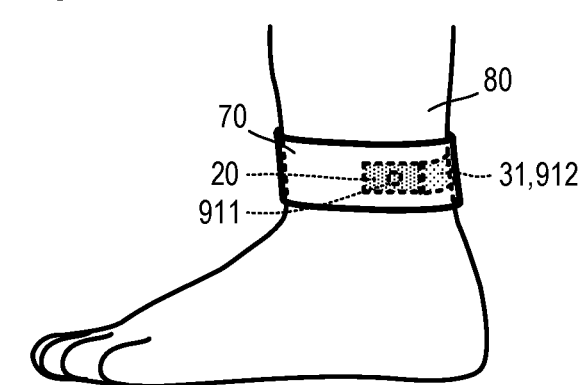
FIG. 4B
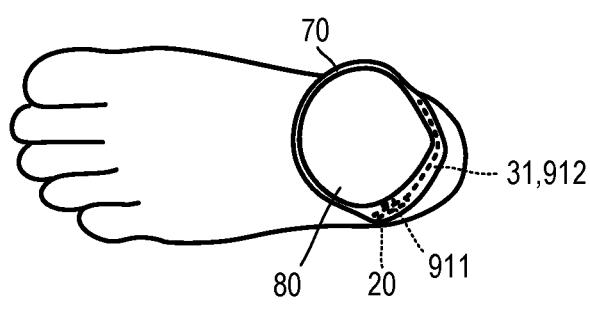
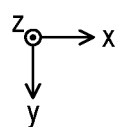

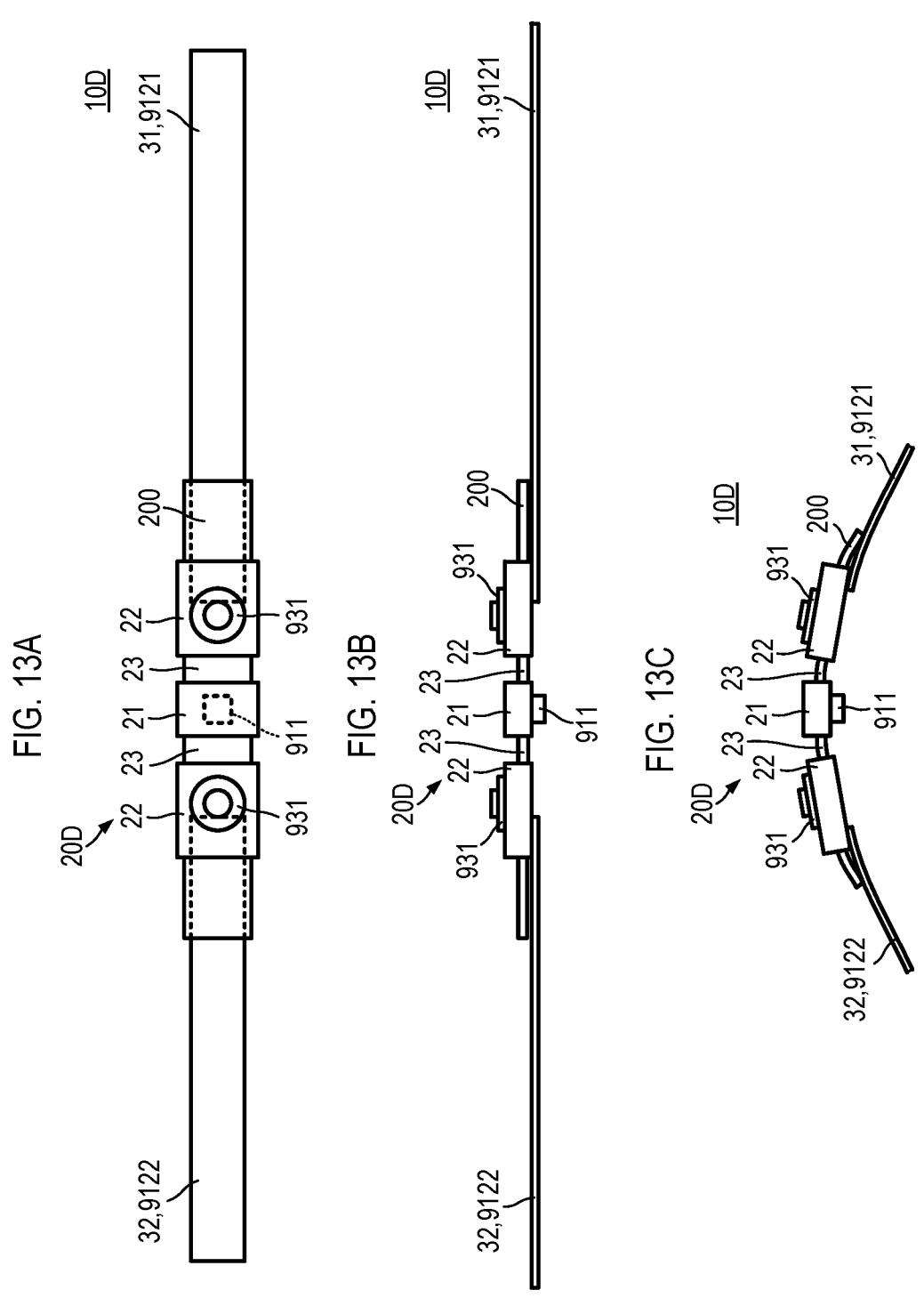

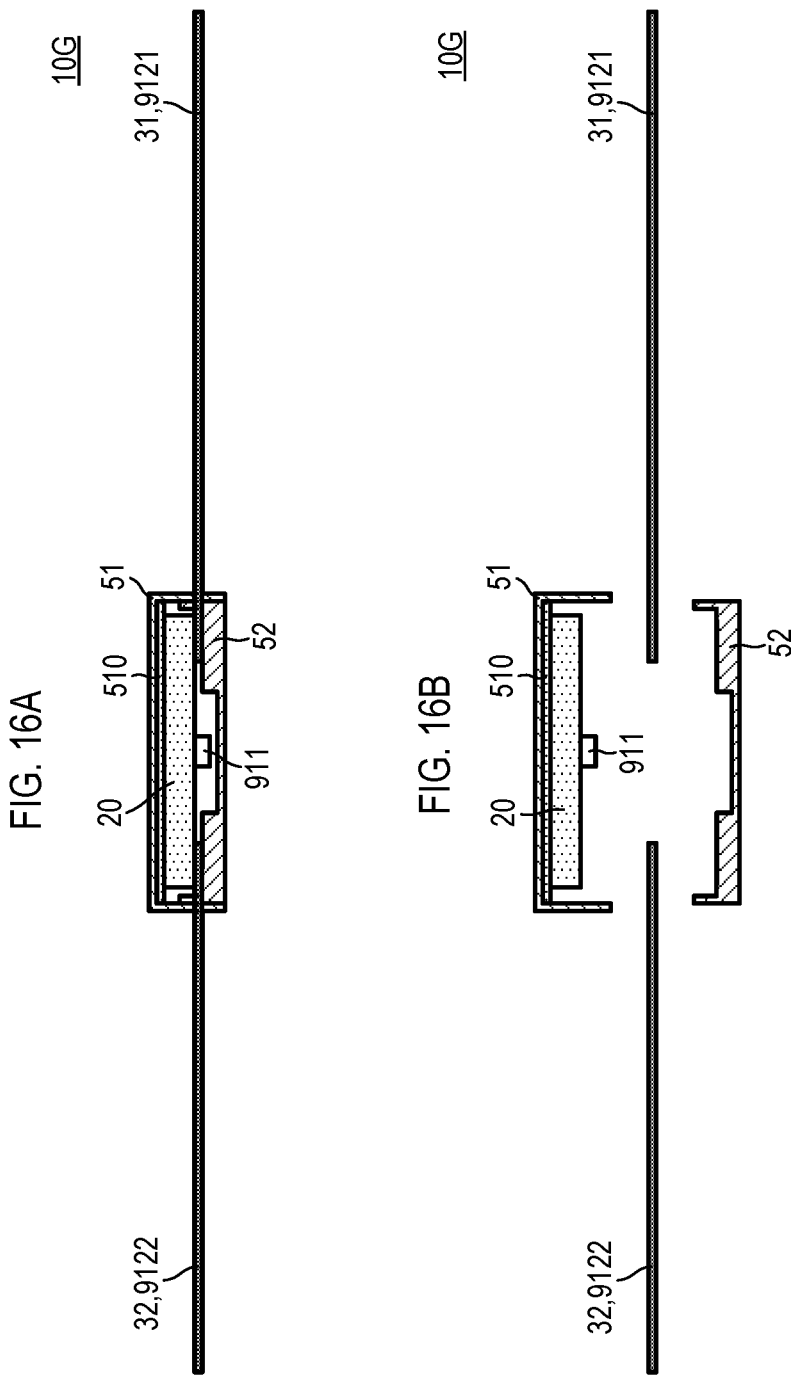

BIOLOGICAL ACTIVITY DETECTION SENSOR

CROSS REFERENCE TO RELATED APPLICATIONS

This application is a continuation of PCT Application No. PCT/JP2021/027852, filed Jul. 28, 2021, which claims priority to Japanese Patent Application No. 2020-129036, filed Jul. 30, 2020, the entire contents of each of which are hereby incorporated by reference in their entirety.

TECHNICAL FIELD

The present invention relates to a biological activity detection sensor that is configured to be worn on a living body, such as a person, and to detect an activity of the living body.

BACKGROUND

Japanese Patent Publication No. 2017-42387 (hereinafter "Patent Literature 1") describes a configuration including a wearable electrode and a biological signal monitoring device. The wearable electrode has a flat film shape and functions as a reception electrode of a myoelectric potential sensor.

As described in Patent Literature 1, the wearable electrode is connected to the biological signal monitoring device via a connecting part. Moreover, the biological signal monitoring device monitors a signal received by the wearable electrode.

However, in the configuration disclosed in Patent Literature 1, since only the myoelectric potential is used, a biological activity may not be accurately detected. Furthermore, it is necessary to directly attach a plurality of wearable electrodes to a living body for myoelectric potential measurement, and the configuration tends to be complicated.

SUMMARY OF THE INVENTION

Therefore, it is an object of the present invention to provide a biological activity detection sensor configured to accurately detect biological activity with a simple configuration.

In an exemplary aspect, a biological activity detection sensor is provided that includes a motion detection sensor that detects a motion of a living body, a tremor sensor that detects a tremor of the living body, and a base member. The base member includes a first member that is deformable in accordance with a mounted state on the living body, and a second member that is less deformable than the first member. The tremor sensor is provided in the first member, and the motion detection sensor is provided in the second member according to the exemplary aspect.

In this configuration, a slight tremor of the living body and a movement of the muscles are accurately detected by the tremor sensor provided in the first member that is easily deformed. Moreover, a larger movement of the living body is accurately detected by the motion detection sensor provided in the second member that is hardly deformed.

According to the exemplary aspects of the present invention, biological activity can be accurately detected with good usability.

BRIEF DESCRIPTION OF DRAWINGS

FIG. 4(A) is a perspective view illustrating an example of an aspect in which the biological activity detection sensor according to the first exemplary embodiment is worn on a subject, and FIG. 4(B) is a plan view thereof.

FIG. 13(A) is a plan view of a sensor part of a biological activity detection sensor according to a fifth exemplary embodiment, FIG. 13(B) is a side view of the sensor part, and FIG. 13(C) is a side view of the sensor part in a curved state.

FIG. 16(A) is a side view of a biological activity detection sensor according to an eighth exemplary embodiment, and FIG. 16(B) is an exploded side view of the biological activity detection sensor according to the eighth exemplary embodiment.

DETAILED DESCRIPTION OF EMBODIMENTS

First Exemplary Embodiment

A biological activity detection sensor according to a first embodiment will be described with reference to the drawings. Hereinafter, a functional configuration (e.g., an electric circuit and/or an electronic circuit configuration) of the biological activity detection sensor will be described, and then a structure of the biological activity detection sensor will be described.

(Functional Configuration of Biological Activity Detection Sensor)

Figure 1:
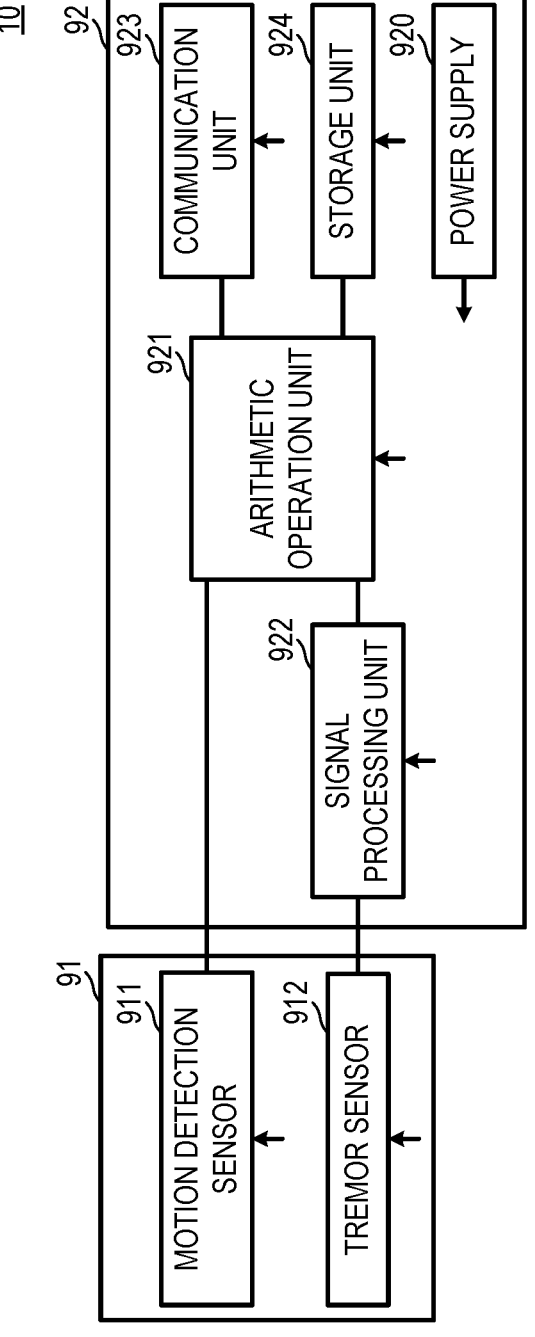
FIG. 1 is a functional block diagram of a biological activity detection sensor according to a first exemplary embodiment.

FIG. 1 is a functional block diagram of a biological activity detection sensor according to a first exemplary embodiment. As illustrated in FIG. 1, a biological activity detection sensor 10 according to the first embodiment generally includes a sensor 91 and a circuit module 92.

The sensor 91 includes a motion detection sensor 911 and a tremor sensor 912. The motion detection sensor 911 and the tremor sensor 912 are connected to the circuit module 92.

The motion detection sensor 911 is configured to detect a motion of a subject and to output a motion detection signal. The subject is a detection target person of a biological activity, and is a wearer of the biological activity detection sensor 10 having a structure that will be described below. In exemplary aspects, the motion detection sensor 911 can be, for example, an acceleration sensor, an angular velocity sensor, a posture sensor, and the like.

The tremor sensor 912 is configured to detect a tremor of the subject and to output a tremor detection signal. In exemplary aspects, the tremor sensor 912 can be, for example, a strain sensor or the like. For purposes of this disclosure, a "tremor" can be considered, for example, an involuntary movement showing rhythmic muscle activity. That is, the tremor is a finely rapid postural tremor observed in a normal person, and is called physiological tremor. For example, the tremor has a frequency of 8 Hz to 12 Hz. Note that a tremor observed in a diseased person such as a Parkinson's patient is a pathological tremor, for example, 4 Hz to 7 Hz, and is not a subject of the "tremor" in the present disclosure. By using tremor, there are the following various advantages over myoelectric potential. For example, the tremor can be detected (e.g., measured) without being directly attached to a surface (e.g., skin or the like) of a subject such as a human body. Muscle stretch can be detected by detecting tremor. By detecting tremor, changes associated with muscle fatigue can be detected.

The circuit module 92 includes a power supply 920, an arithmetic operation unit 921, a signal processing unit 922, a communication unit 923, and a storage unit 924. The power supply 920 can be, for example, a battery such as a secondary battery or a primary battery. The arithmetic operation unit 921 can be, for example, a microcomputer or the like. The signal processing unit 922 can be, for example, an analog or digital electronic circuit. The communication unit 923 can be, for example, analog and digital electronic circuits. The storage unit 924 can be, for example, a storage medium such as an SSD, a memory card, a reading mechanism thereof, and the like. Preferably, these functional units are small and light to such an extent that they hardly cause a load in wearing of the subject.

In operation, the power supply 920 supplies power to the arithmetic operation unit 921, the signal processing unit 922, the communication unit 923, and the storage unit 924, and supplies power to the motion detection sensor 911 and the tremor sensor 912 of the sensor 91.

The signal processing unit 922 amplifies the tremor detection signal, performs filter processing, and the like, and outputs the signal to the arithmetic operation unit 921.

Moreover, the arithmetic operation unit 921 generates biological activity detection information using the motion detection signal and the tremor detection signal after the signal processing in the signal processing unit 922. The biological activity detection information is, for example, movement, posture, and the like, at a predetermined site of the subject. At this time, by using the motion detection signal and the tremor detection signal, the arithmetic operation unit 921 can be configured to detect the biological activity with higher accuracy than using only the myoelectric potential.

For example, the arithmetic operation unit 921 removes noise included in the tremor detection signal on the basis of the motion detection signal. As a result, the biological activity detection information is more accurate. Furthermore, the arithmetic operation unit 921 detects a type, a magnitude, and the like of the biological activity from a combination of the tremor detection signal and the motion detection signal. As a result, the biological activity detection information is more accurate.

In an exemplary aspect, the communication unit 923 can be configured to transmit the biological activity detection information to an external personal computer, smartphone, server, or the like. The storage unit 924 stores, for example, the biological activity detection information. As a communication (e.g., transmission) means of the communication unit 923, a wireless LAN, data communication using a mobile phone line, Bluetooth®, or the like can be used. Note that the communication unit 923 may not be provided, and data of the biological activity detection information may be transferred to the outside via a memory card disposed in the storage unit 924 according to another exemplary aspect.

(Structure of Biological Activity Detection Sensor)

Figure 2A:
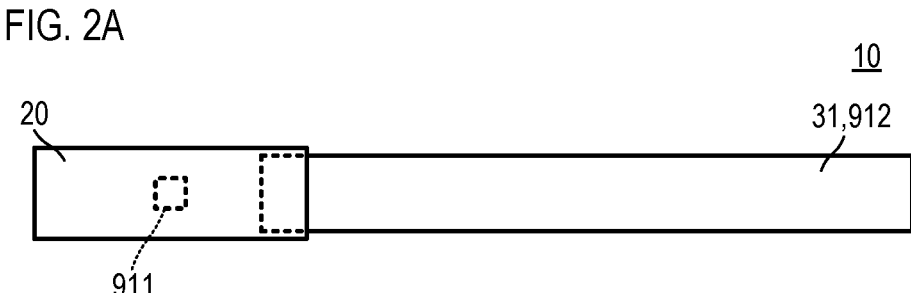
FIG. 2(A) is a plan view of the biological activity detection sensor according to the first exemplary embodiment.
Figure 2B:
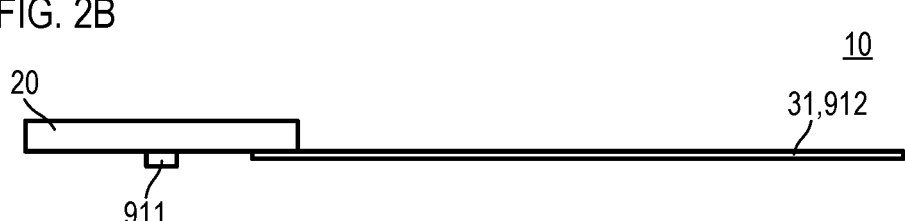
FIG. 2(B) is a side view of the biological activity detection sensor according to the first exemplary embodiment.

FIG. 2(A) is a plan view of the biological activity detection sensor according to the first exemplary embodiment, and FIG. 2(B) is a side view of the biological activity detection sensor according to the first exemplary embodiment. Note that FIGS. 2(A) and 2(B) schematically illustrate an aspect of a connecting part between a first member and a second member, and specific examples thereof are illustrated in FIGS. 5(A), 5(B), 5(C), and 5(D) described below.

As illustrated in FIGS. 2(A) and 2(B), the biological activity detection sensor 10 includes a second member 20 and a first member 31.

The second member 20 is a flat plate having a rectangular shape in plan view.

A main body of the second member 20 is, for example, an insulating substrate having a predetermined thickness. The main body of the second member 20 is, for example, an insulating resin substrate such as FR4, and has predetermined rigidity. That is, the second member 20 is formed mainly of a so-called rigid substrate (e.g., a solid substrate).

The functional components forming the circuit module 92 described above are built in, formed on, or mounted on the second member 20. It is noted that the detail illustration of this configuration is omitted in FIGS. 2(A) and 2(B).

The motion detection sensor 911 is mounted on one principal surface of the second member 20 and can be a so-called surface-mountable chip component according to an exemplary aspect.

The first member 31 is a rectangular flat film having a longitudinal direction and a lateral direction in plan view.

Here, the flat film is thinner than the flat plate forming the second member 20 and has flexibility.

A main body of the first member 31 is, for example, a dielectric film, and is more easily deformable than the second member 20. In other words, the first member 31 is formed of a first material that has a Young's modulus lower than that of a second material that forms the second member 20. That is, the main body of the first member 31 is a so-called flexible substrate.

A primary or main material of the first member 31 is, for example, a piezoelectric material, such as polylactic acid, that generates electric charges by stress in a predetermined direction. That is, the main body of the first member 31 is a piezoelectric film.

An electrode that detects a potential difference (e.g., a voltage) generated by the electric charges is formed in the first member 31. With this configuration, the first member 31 also functions as the tremor sensor 912 including a piezoelectric sensor.

The second member 20 and the first member 31 are electrically and physically connected. More specifically, one end in the longitudinal direction of the first member 31 is connected to a mounting surface of the motion detection sensor 911 in the second member 20. As a result, the biological activity detection sensor 10 has a belt-like shape.
(Aspect of Wearing on Subject)

Figure 3:
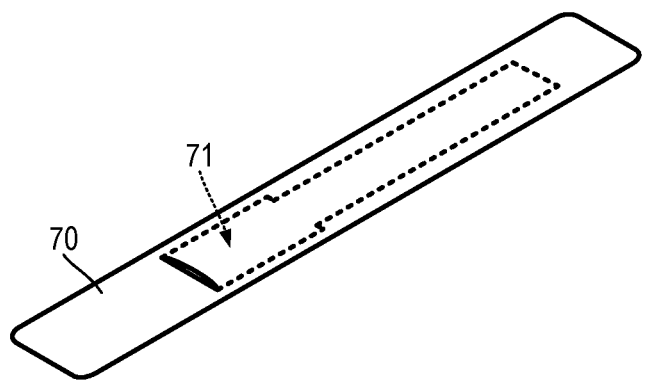
FIG. 3 is an external perspective view of a mounting member according to the first exemplary embodiment.

FIG. 3 is an external perspective view of a mounting member according to the first embodiment. FIG. 4(A) is a side view illustrating an example of an aspect in which the biological activity detection sensor according to the first embodiment is worn on a subject, and FIG. 4(B) is a plan view thereof.

As illustrated in FIG. 3, a mounting member 70 has an elongated shape having a longitudinal direction and a lateral direction. The mounting member 70 has flexibility. The mounting member 70 should be at least more easily deformable than the second member 20 of the biological activity detection sensor 10, and it is preferable if the mounting member 70 deforms as easily as the first member 31 or is more easily deformable than the first member 31. In exemplary aspects, a material of the mounting member 70 is, for example, chemical fibers such as polyester, nylon, and polyurethane, or natural fibers such as cotton.

Locking members (for example, a hook-and-loop fastener, such as Velcro®, and the like, that are capable of locking the surfaces of the mounting member 70 to each other are installed near both ends in the longitudinal direction of the mounting member 70. Thus, the mounting member 70 can maintain an annular shape when attached to a user's limb (e.g., ankle), for example.

As further shown, the mounting member 70 has a substantially rectangular and elongated pocket 71. One end of the pocket 71 in the longitudinal direction is open. The biological activity detection sensor 10 is inserted into the pocket 71. By making the shape of the pocket 71 substantially the same as that of the biological activity detection sensor 10, the biological activity detection sensor 10 is installed in a substantially constant state with respect to the mounting member 70.

As described above, the biological activity detection sensor 10 installed on the mounting member 70 is wound around an ankle 80 of the subject as illustrated in FIGS. 4(A) and 4(B), for example. At this time, the mounting member 70 is mounted on the ankle 80 such that the first member 31 of the biological activity detection sensor 10, that is, the tremor sensor 912 overlaps a tendon (for example, the Achilles tendon) to be detected when viewed from a side (e.g., viewed in an X direction). More specifically, the mounting member 70 is mounted on the ankle 80 such that the longitudinal direction of the first member 31 (e.g., the tremor sensor 912) is orthogonal to an extending direction of the Achilles tendon.

With such a configuration, the tremor sensor 912 can detect a tremor of a target site, for example, the Achilles tendon as shown in FIGS. 4(A) and 4(B) of the subject. At this time, the tremor sensor 912 can be provided as the first member 31 having low rigidity and being easily deformed. Therefore, the tremor sensor 912 is disposed so as to follow an outer shape of the target site. As a result, the tremor sensor 912 can detect the target site tremor of the subject with high accuracy. Moreover, the tremor sensor 912 is fixed at a stable position with respect to the target site by the mounting member 70 that is easily deformed. As a result, the tremor sensor 912 is disposed to more accurately follow the outer shape of the target site, and the tremor can be detected more accurately and more reliably.

Furthermore, with this configuration, since the motion detection sensor 911 is fixed in the vicinity of the target site of the subject, the motion of the target site of the subject can be detected with high accuracy. Moreover, the motion detection sensor 911 is disposed on the second member 20 having higher rigidity and less deformation than the first member 31. As a result, the motion detection sensor 911 can suppress an influence of an undesired stress on the motion detection signal. For example, when the motion detection sensor 911 is disposed on a deformable member, the motion detection sensor 911 generates a motion detection signal including stress due to the deformation. However, in this configuration, since the second member 20 is hardly deformed, the motion detection sensor 911 can accurately reflect the motion of the target site of the subject and generate the motion detection signal in which the influence of the undesirable stress is suppressed. That is, the motion detection sensor 911 can detect the motion of the target site of the subject with high accuracy.

As such, the biological activity detection sensor 10 is configured to generate highly accurate biological activity detection information by these operational effects.

Furthermore, in the above configuration, the circuit module is formed in the second member 20. That is, the circuit module is formed on the second member 20 on which the biological activity detection sensor 10 is mounted. Therefore, the biological activity detection sensor 10 can be downsized as compared with a case where the circuit module is formed on a substrate or the like different from the second member 20 on which the biological activity detection sensor is mounted, and the biological activity detection sensor 10 can be downsized. As a result, the biological activity detection sensor 10 can suppress discomfort or the like when worn by the subject.

Furthermore, in the above-described configuration, since the tremor sensor 912 has a flat film shape, sensing can be performed on a plane. This configuration can suppress deterioration of detection sensitivity or the like due to positional deviation at the time of wearing, and can improve robustness against positional deviation at the time of wearing.

Furthermore, in the above-described configuration, since the tremor sensor 912 is a strain sensor, the tremor sensor 912 may not be brought into direct contact with a surface of the skin of the subject. Therefore, it is possible to provide a variety of aspects of being worn on the subject.
(Specific Example of Connection Aspect Between Second Member 20 and First Member 31)

FIGS. 5(A), 5(B), 5(C), and 5(D) are enlarged side views illustrating exemplary connection aspects between a first member and a second member.

Figure 5A:
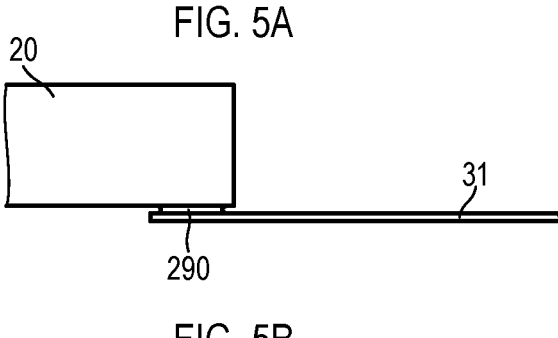
FIGS. 5(A), 5(B), 5(C), and 5(D) are enlarged side views illustrating a connection aspect between a first member and a second member.

In the aspect illustrated in FIG. 5(A), the second member 20 and the first member 31 are connected by a conductive bonding material 290. More specifically, an electrode pattern formed on the second member 20 and an electrode pattern formed on the first member 31 are connected by the conductive bonding material 290 such as solder.

Figure 5B:
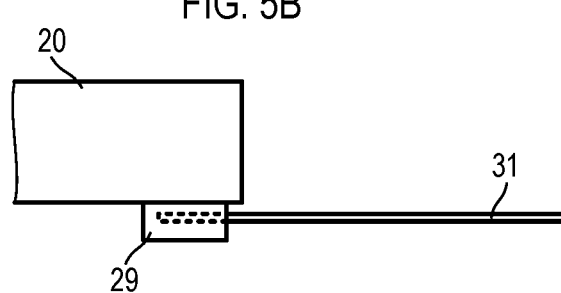

In the aspect illustrated in FIG. 5(B), a first member insertion fitting member 29 is mounted on the second member 20. The first member insertion fitting member 29 can be provided as, for example, a connector member. The first member 31 is inserted and fitted into the first member insertion fitting member 29. As a result, the second member 20 and the first member 31 are connected.

Figure 5C:
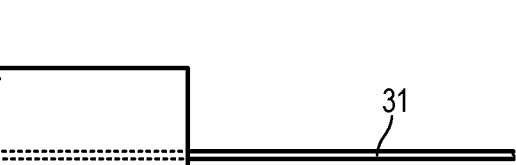

In the aspect illustrated in FIG. 5(C), the second member 20 is a stack body in which a plurality of insulator layers are stacked. The first member 31 is a part of the plurality of insulator layers. That is, the second member 20 and the first member 31 collectively form a rigid-flexible substrate having a rigid part and a flexible part. As a result, the second member 20 and the first member 31 are connected. Note that, in this case, the second member 20 and the first member 31 may be made of the same material, for example, liquid crystal polymer, polyimide, or the like, according to an exemplary aspect.

Figure 5D:
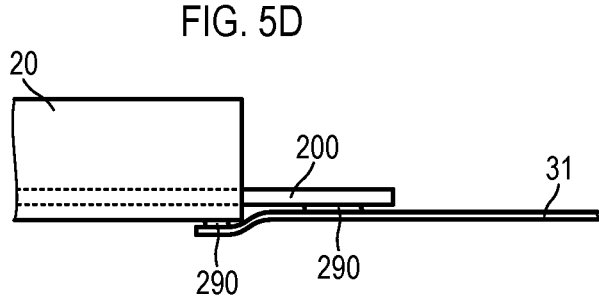

In the aspect illustrated in FIG. 5(D), the second member 20 is a stack body in which a plurality of insulator layers are stacked. The second member 20 includes a flexible layer 200. That is, the second member 20 is a so-called rigid-flexible substrate. The first member 31 is connected to the second member 20 by a conductive bonding material, and is also connected to the flexible layer 200 by a conductive bonding material. Note that the first member 31 may be connected only to the flexible layer 200.

In each of the above exemplary aspects, the second member 20 and the first member 31 can be electrically and physically connected.

Second Exemplary Embodiment

Figure 6:
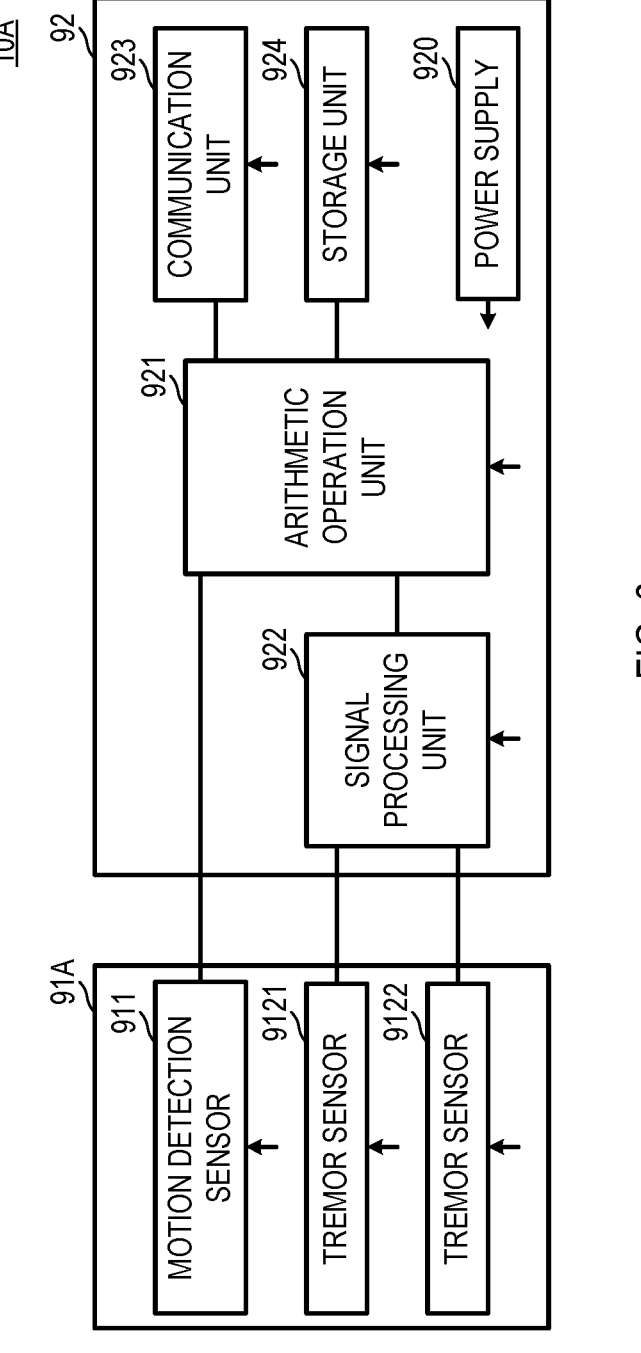
FIG. 6 is a functional block diagram of a biological activity detection sensor according to a second exemplary embodiment.
Figures 7A, 7B:
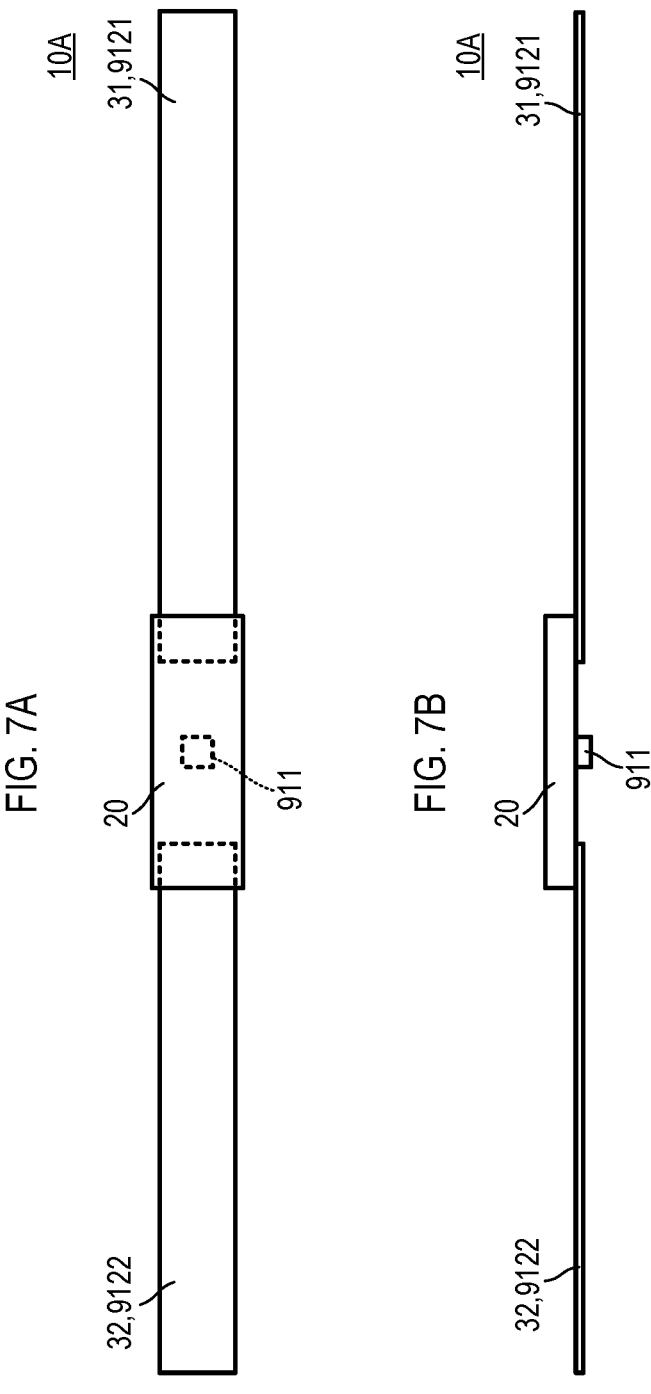
FIG. 7(A) is a plan view of the biological activity detection sensor according to the second exemplary embodiment.
FIG. 7(B) is a side view of the biological activity detection sensor according to the second exemplary embodiment.

A biological activity detection sensor according to a second exemplary embodiment will be described with reference to the drawings. FIG. 6 is a functional block diagram of a biological activity detection sensor according to the second exemplary embodiment. FIG. 7(A) is a plan view of the biological activity detection sensor according to the second embodiment, and FIG. 7(B) is a side view of the biological activity detection sensor according to the second embodiment.

As illustrated in FIG. 6, functionally, the biological activity detection sensor 10A according to the second exemplary embodiment is different from the biological activity detection sensor 10 according to the first embodiment in a configuration of the sensor 91A. Other configurations of the biological activity detection sensor 10A are similar to those of the biological activity detection sensor 10 as described above, and description of similar parts is omitted.

In particular, the sensor 91A includes a motion detection sensor 911, a tremor sensor 9121 (e.g., a first tremor sensor), and a tremor sensor 9122 (e.g., a second tremor sensor). That is, the sensor 91A includes two tremor sensors.

A signal processing unit 922 performs signal processing on a tremor detection signal of the tremor sensor 9121 and a tremor detection signal of the tremor sensor 9122, and outputs the processed signals to an arithmetic operation unit 921. The arithmetic operation unit 921 generates biological activity detection information by using a motion detection signal, the tremor detection signal of 9121, and the tremor detection signal of the tremor sensor 9122.

As illustrated in FIGS. 7(A) and 7(B), the biological activity detection sensor 10A according to the second embodiment is structurally different from the biological activity detection sensor 10 according to the first embodiment in that a plurality of first members are provided. Other configurations of the biological activity detection sensor 10A are similar to those of the biological activity detection sensor 10 as described above, and description of similar parts is omitted.

As shown, the biological activity detection sensor 10A includes a first member 31 and a first member 32. In the exemplary aspect, the first member 31 and the first member 32 are made of the same material. Moreover, the first member 31 and the first member 32 have the same or similar shapes, and both have a longitudinal direction.

In this aspect, the first member 31 functions as the tremor sensor 9121 and the first member 32 functions as the tremor sensor 9122.

The first member 31 is connected to the vicinity of one end of the second member 20. More specifically, one end in the longitudinal direction of the first member 31 is connected to the vicinity of one end of the second member 20. The first member 32 is connected to the vicinity of the other end of the second member 20. More specifically, one end in the longitudinal direction of the first member 32 is connected to the vicinity of the other end of the second member 20.

With this configuration, the first member 31 and the first member 32 are disposed with the second member 20 interposed therebetween. Furthermore, the first member 31 and the first member 32 are disposed such that longitudinal directions thereof are substantially parallel to each other. Therefore, the biological activity detection sensor 10A has a band shape in which the first member 31, the second member 20, and the first member 32 are connected in this order.

With such a configuration, the biological activity detection sensor 10A can detect tremors of a plurality of sites of the subject.

(Aspect of Wearing on Subject)

Figure 8:
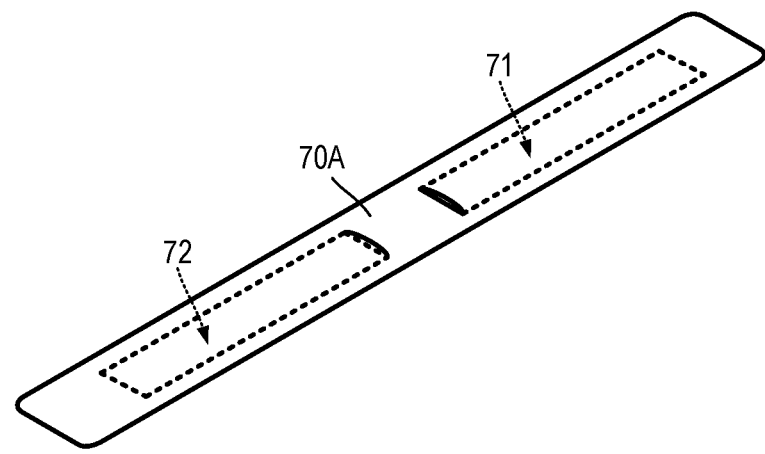
FIG. 8 is an external perspective view of a mounting member according to the second exemplary embodiment.
Figure 9A:
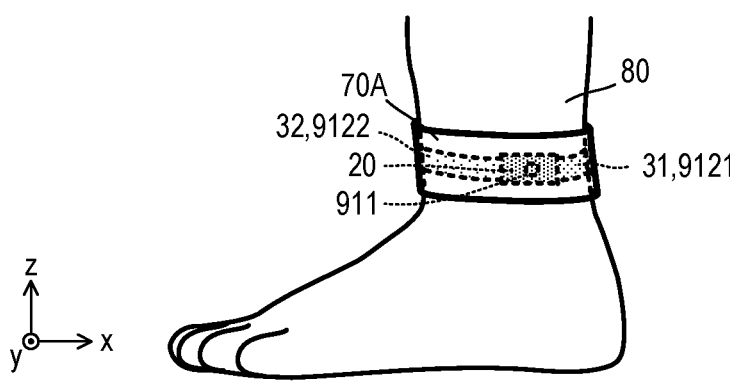
FIG. 9(A) is a perspective view illustrating an example of an aspect in which the biological activity detection sensor according to the second exemplary embodiment is worn on a subject.
Figure 9B:
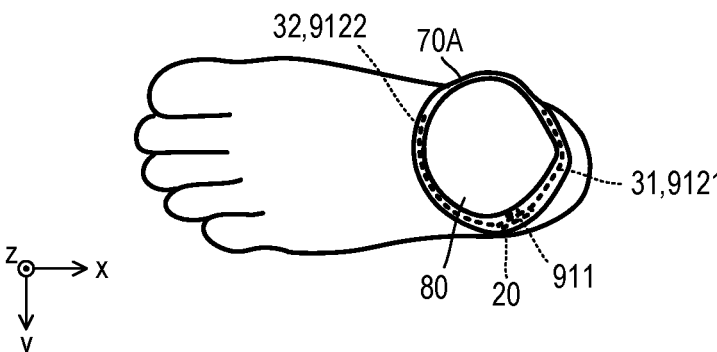
FIG. 9(B) is a plan view thereof.

FIG. 8 is an external perspective view of a mounting member according to the second exemplary embodiment. Moreover, FIG. 9(A) is a side view illustrating an example of an aspect in which the biological activity detection sensor according to the second exemplary embodiment is worn on the subject, and FIG. 9(B) is a plan view thereof.

As illustrated in FIG. 8, a mounting member 70A has an elongated shape having a longitudinal direction and a lateral direction. The mounting member 70A has flexibility. In this aspect, the mounting member 70A should be at least more easily deformable than the second member 20 of the biological activity detection sensor 10A, and it is preferably if the mounting member 70A deforms as easily as the first member 31 and the first member 32 or is more easily deformable than the first member 31 and the first member 32.

The mounting member 70A has a pocket 71 and a pocket 72 that are substantially rectangular and elongated. First ends in a longitudinal direction of the pocket 71 and the pocket 72 are opened. The pocket 71 and the pocket 72 are arranged side by side in the longitudinal direction of the mounting member 70. An opening of the pocket 71 and an opening of the pocket 72 face each other.

The first member 31 of the biological activity detection sensor 10A is inserted into the pocket 71, and the first member 32 of the biological activity detection sensor 10A is inserted into the pocket 72. By making the shape of the pocket 71 substantially the same as that of the first member 31 and making the shape of the pocket 72 substantially the same as that of the first member 32, the biological activity detection sensor 10A is installed in a substantially constant state with respect to the mounting member 70A.

As described above, the biological activity detection sensor 10 installed on the mounting member 70A is wound around an ankle 80 of the subject as illustrated in FIGS. 9(A) and 9(B), for example. At this time, the mounting member 70A is mounted on the ankle 80 such that the first member 31 of the biological activity detection sensor 10A, that is, the tremor sensor 9121 overlaps a site to be detected (for example, the Achilles tendon) when viewed from a side (viewed in an X direction). Alternatively, the mounting member 70A is mounted on the ankle 80, such that the first member 32 of the biological activity detection sensor 10A, that is, the tremor sensor 9122 overlaps another site (for example, the tibialis anterior muscle) to be detected when viewed from a side (viewed in the X direction).

With such a configuration, the tremor sensor 9121 and the tremor sensor 9122 can be configured to detect tremors of the plurality of target sites, for example, the Achilles tendon and the tibialis anterior muscle, respectively, of the subject as shown in FIGS. 9(A) and 9(B). At this time, the tremor sensor 9121 can be provided as the first member 31 having low rigidity and being easily deformed. Therefore, the tremor sensor 9121 can detect a tremor with high accuracy. Moreover, the tremor sensor 9121 is fixed at a stable position with respect to the target site by the mounting member 70A which is easily deformed. As a result, the tremor sensor 9121 can detect a tremor with higher accuracy and more reliably.

Similarly, the tremor sensor 9122 can be provided as the first member 32 having low rigidity and being easily deformed. Therefore, the tremor sensor 9122 can detect a tremor with high accuracy. Moreover, the tremor sensor 9122 is fixed at a stable position with respect to the target site by the mounting member 70A which is easily deformed. As a result, the tremor sensor 9122 can detect a tremor with higher accuracy and more reliably.

As described above, the biological activity detection sensor 10A is configured to detect the tremors at the plurality of sites, and to generate biological activity detection information using the tremor detection signals at the plurality of sites. Therefore, the biological activity detection sensor 10A can generate highly accurate biological activity detection information with more complicated contents.

Third Exemplary Embodiment

Figure 10:
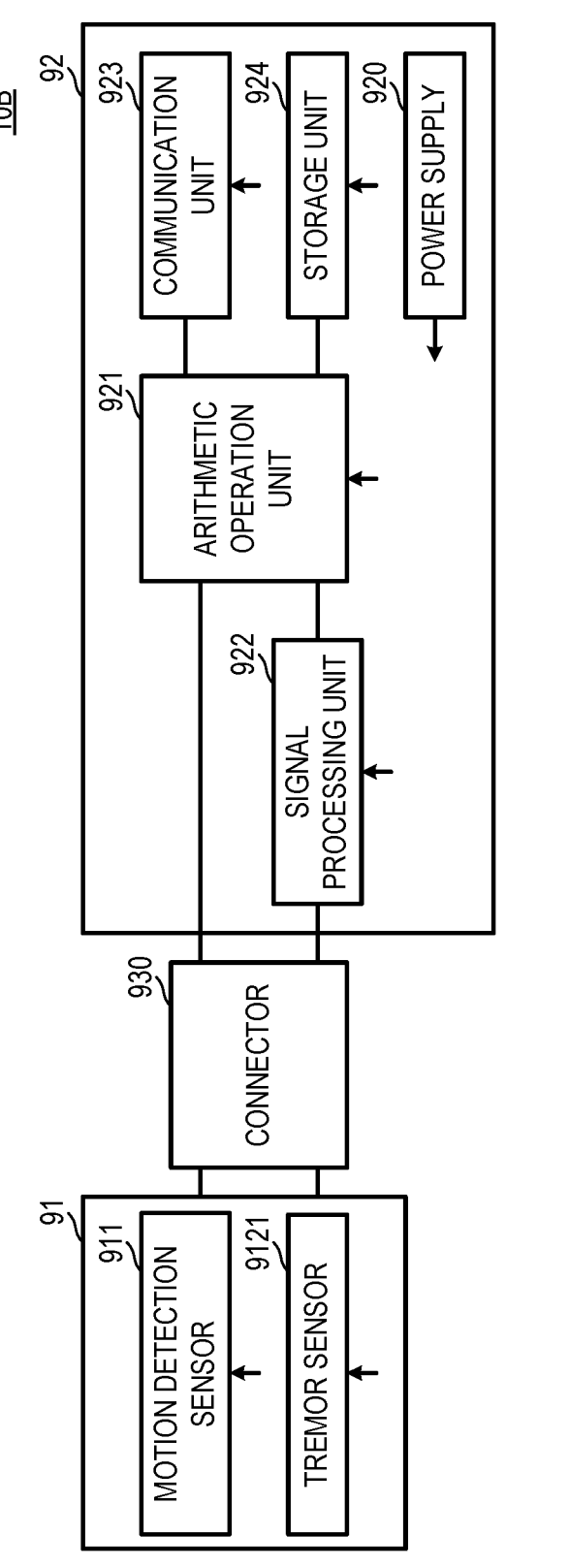
FIG. 10 is a functional block diagram of a biological activity detection sensor according to a third exemplary embodiment.
Figures 11A, 11B, 11C:
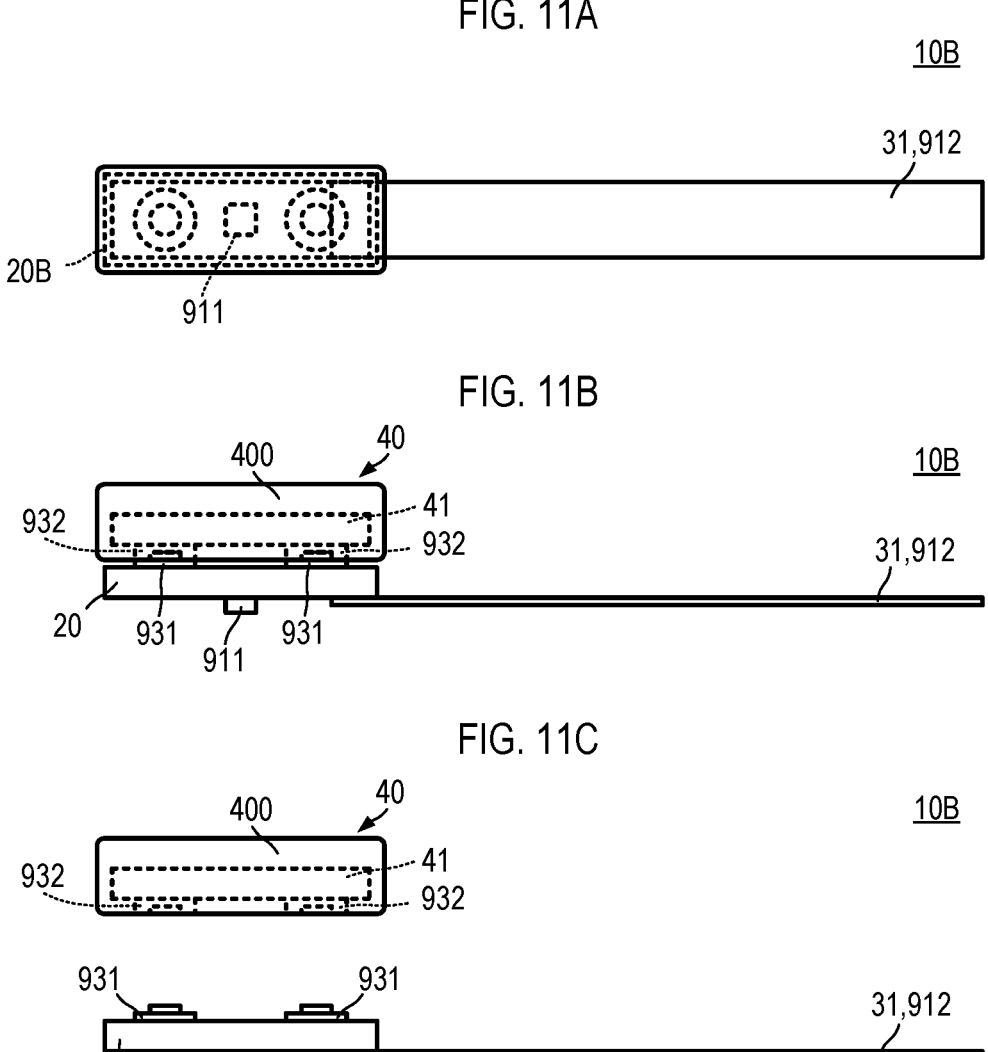
FIG. 11(A) is a plan view of the biological activity detection sensor according to the third exemplary embodiment.
FIG. 11(B) is a side view of the biological activity detection sensor according to the third exemplary embodiment.
FIG. 11(C) is an exploded side view of the biological activity detection sensor according to the third exemplary embodiment.

A biological activity detection sensor according to a third exemplary embodiment will be described with reference to the drawings. FIG. 10 is a functional block diagram of a biological activity detection sensor according to a third exemplary embodiment. FIG. 11(A) is a plan view of the biological activity detection sensor according to the third exemplary embodiment, FIG. 11(B) is a side view of the biological activity detection sensor according to the third exemplary embodiment, and FIG. 11(C) is an exploded side view of the biological activity detection sensor according to the third exemplary embodiment.

As illustrated in FIG. 10, functionally, a biological activity detection sensor 10B according to the third embodiment is different from the biological activity detection sensor 10 according to the first embodiment in a connection component/aspect between a sensor 91 and a circuit module 92. Other configurations of the biological activity detection sensor 10B are similar to those of the biological activity detection sensor 10, and description of similar parts is omitted.

In particular, the biological activity detection sensor 10B includes a connector 930. In this aspect, the connector 930 is configured to detachably connect the sensor 91 and the circuit module 92.

As illustrated in FIGS. 11(A), 11(B), and 11(C), the biological activity detection sensor 10B according to the third embodiment is structurally different from the biological activity detection sensor 10 according to the first embodiment in that the circuit module 92 is formed separately from a second member 20 and a package component 40 that realizes the circuit module 92 is provided. Other configurations of the biological activity detection sensor 10B are similar to those of the biological activity detection sensor 10 as described above, and description of similar parts is omitted.

The biological activity detection sensor 10B includes the second member 20, a first member 31, and the package component 40.

The circuit module 92 is not formed in the second member 20. A connector member 931 is mounted on a principal surface of the second member 20 opposite to a mounting surface of the motion detection sensor 911.

In plan view of the second member 20, the connector member 931 does not overlap with the motion detection sensor 911.

The package component 40 includes a circuit board 41, a housing 400, and a connector member 932. The circuit module 92 is formed on the circuit board 41. The connector member 932 is mounted on one principal surface of the circuit board 41. The circuit board 41 and the connector member 932 are accommodated in the housing 400. At this time, the connector member 932 is accommodated in the housing 400 such that a connection surface to the outside is exposed to the outside.

The connector member 931 and the connector member 932 are electrically and physically connected by fitting.

As described above, the biological activity detection sensor 10B can separate the belt-shaped structure that is provided as the sensor 91 and the structure that is provided as the circuit module 92.

With this configuration, the package component 40 for providing the circuit module 92 can be replaced while mounting the belt-shaped structure that provides for the sensor 91. Furthermore, the belt-shaped structure that can be provided as the sensor 91 and the package component 40 that can be provided as the circuit module 92 can be individually replaced. As a result, replacement at the time of failure and replacement for hygiene control can be efficiently realized.

Furthermore, with this configuration, the circuit module 92 can be removed from the band-shaped structure, and the power supply 920 of the circuit module 92 can be charged. As a result, usability of the biological activity detection sensor 10B can be improved.

Furthermore, in this configuration, the connector member 931 is mounted on the second member 20 that is hardly deformed and has high rigidity. Accordingly, separation can be suppressed between the connector member 932 and the second member 20 due to attachment and detachment of the connector member 931 to and from the connector member 931. Therefore, the biological activity detection sensor 10B can improve structural reliability.

Furthermore, in this configuration, the connector member 931 does not overlap the motion detection sensor 911 in plan view. As a result, an impact generated at the time of attaching and detaching the connector member 931 and the connector member 932 can be prevented from being applied to the motion detection sensor 911.

Note that, in the configuration of the present embodiment, a part of the circuit module 92 may be formed in the second member 20, and the other part may be formed in the package component 40. In this case, for example, an amplifier circuit, a filter circuit, or the like of the signal processing unit 922 in the circuit module 92 can be formed in the second member 20. As a result, for example, in the case of forming the amplifier circuit, it is possible to suppress transmission of a motion detection signal or a tremor detection signal (particularly, a tremor detection signal) having a small amplitude via the connector member 931 and the connector member 932. Furthermore, in the case of forming the filter circuit, a motion detection signal and a tremor detection signal in a state where noise is suppressed can be transmitted via the connector member 931 and the connector member 932.

Fourth Exemplary Embodiment

Figure 12:
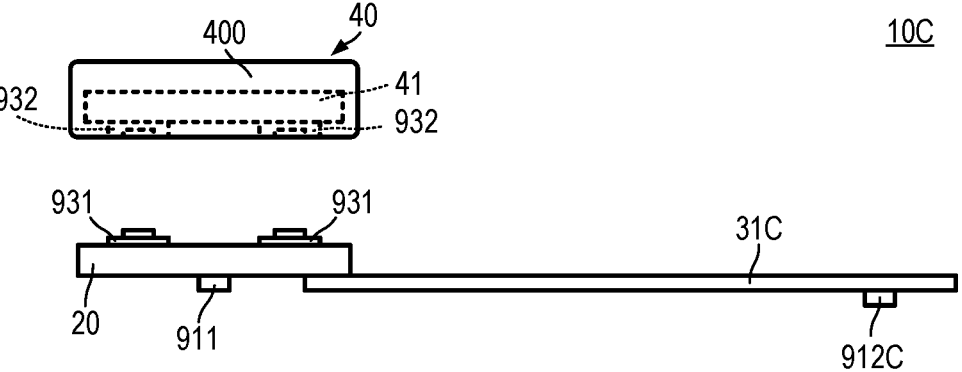
FIG. 12 is an exploded side view of a biological activity detection sensor according to a fourth exemplary embodiment.

A biological activity detection sensor according to a fourth exemplary embodiment will be described with reference to the drawings. FIG. 12 is an exploded side view of a biological activity detection sensor according to a fourth exemplary embodiment.

As illustrated in FIG. 12, a biological activity detection sensor 10C according to the fourth embodiment is different from the biological activity detection sensor 10B according to the third embodiment in the configurations of a first member 31C and a tremor sensor 912C. Other configurations of the biological activity detection sensor 10C are similar to those of the biological activity detection sensor 10B, and description of similar parts is omitted.

As shown, the biological activity detection sensor 10C includes the first member 31C. In an exemplary aspect, the first member 31C is made of a deformable material such as PET, PEN, PI, or liquid crystal polymer, and has almost no piezoelectricity.

In an exemplary aspect, the tremor sensor 912C can be a chip component such as an acceleration sensor. Moreover, the tremor sensor 912C is mounted on the first member 31C.

With this configuration, the biological activity detection sensor 10C can achieve the same effects as those of the biological activity detection sensor 10B.

Fifth Exemplary Embodiment

A biological activity detection sensor according to a fifth exemplary embodiment will be described with reference to the drawings. FIG. 13(A) is a plan view of a sensor part of a biological activity detection sensor according to a fifth exemplary embodiment, FIG. 13(B) is a side view of the sensor part, and FIG. 13(C) is a side view of the sensor part in a curved state. Note that in FIGS. 13(A), 13(B), and 13(C), the description of a package component 40 forming a circuit module 92 is omitted.

As illustrated in FIGS. 13(A), 13(B), and 13(C), a biological activity detection sensor 10D according to the fifth embodiment is different from the biological activity detection sensor 10B according to the third embodiment in that a plurality of first members and a second member 20D are provided. In other words, the biological activity detection sensor 10D is different in that the second member 20D is adopted instead of the second member 20 in a state where the configuration of the biological activity detection sensor 10A is applied to the biological activity detection sensor 10B. Other configurations of the biological activity detection sensor 10D are similar to those of the biological activity detection sensor 10B, and description of similar parts is omitted.

In this exemplary aspect, the second member 20D includes a rigid part 21, two rigid parts 22, and a flexible part 23. The rigid part 21 and the rigid parts 22 are made of, for example, an insulating resin substrate or the like having high rigidity such as FR4, and the flexible part 23 is made of an insulating resin film or the like having low rigidity such as PET or PEN.

The rigid part 21 and the two rigid parts 22 are arranged side by side in one direction. The rigid part 21 is disposed at a position sandwiched between the two rigid parts 22 in a longitudinal direction. The rigid part 21 and the two rigid parts 22 are connected to each other by the flexible part 23. That is, the second member 20D is a so-called rigid-flexible substrate.

As further shown, a motion detection sensor 911 is mounted on the rigid part 21. A first member 31 is connected to the one rigid part 22, and a connector member 931 is mounted. A first member 32 is connected to the other rigid part 22, and a connector member 931 is mounted.

With this configuration, the biological activity detection sensor 10D can exhibit the same operation and effect as the biological activity detection sensor 10B. Moreover, with this configuration, as illustrated in FIG. 13(C), by curving the flexible part 23, the biological activity detection sensor 10D can be disposed such that the second member 20D also draws a substantially curved surface. As a result, the biological activity detection sensor 10D can be disposed in a state of further following an outer shape of the target site of the subject. Therefore, the discomfort at the time of wearing of the subject can be reduced.

Furthermore, in this configuration, the rigid part 21 on which the motion detection sensor 911 is mounted and the rigid part 22 on which the connector member 931 is mounted are different from each other. As a result, it is possible to further suppress an impact at the time of attaching and detaching the connector member 931 from being applied to the motion detection sensor 911.

Sixth Exemplary Embodiment

Figures 14A, 14B:
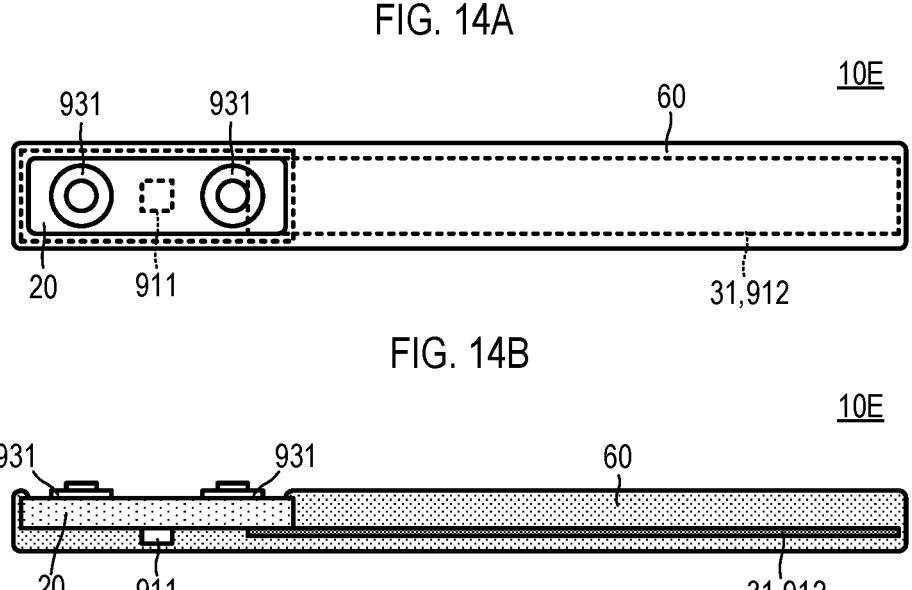
FIG. 14(A) is a plan view of a sensor part of a biological activity detection sensor according to a sixth exemplary embodiment.
FIG. 14(B) is a side view of a sensor part of the biological activity detection sensor according to the sixth exemplary embodiment.

A biological activity detection sensor according to a sixth exemplary embodiment will be described with reference to the drawings. FIG. 14(A) is a plan view of a sensor part of a biological activity detection sensor according to a sixth exemplary embodiment, and FIG. 14(B) is a side view of a sensor part of the biological activity detection sensor according to the sixth exemplary embodiment. Note that, in FIGS. 14(A) and 14(B), the description of a package component 40 forming a circuit module 92 is omitted.

As illustrated in FIGS. 14(A) and 14(B), a biological activity detection sensor 10E according to the sixth embodiment is different from the biological activity detection sensor 10B according to the third embodiment in that an insulating protective layer 60 is provided. Other configurations of the biological activity detection sensor 10E are similar to those of the biological activity detection sensor 10B, and description of similar parts will be omitted.

The biological activity detection sensor 10E includes the insulating protective layer 60. The insulating protective layer 60 covers an entire surface of a second member 20 excluding a mounting surface of a connector member 931, and an entire surface of a first member 31. Note that the insulating protective layer 60 may cover a part of the second member 20 on a side of the mounting surface of the connector member 931 as long as the connector member 931 is exposed so as to be fittable to a connector member 932.

It is more preferable that the insulating protective layer 60 has lower rigidity than the second member 20, and has the same level of rigidity as the first member 31 or lower rigidity than the first member 31.

With this configuration, the biological activity detection sensor 10E achieves the same effects as those of the biological activity detection sensor 10B. Moreover, with this configuration, the biological activity detection sensor 10E can improve waterproofness and durability of the second member 20, the motion detection sensor 911, and the first member 31. Therefore, when a member, such as the mounting member 70 of the first embodiment, is attached to the first member 31 in the biological activity detection sensor 10E, washing can be performed in a state where the mounting member 70 is mounted on the first member 31.

Seventh Exemplary Embodiment

Figures 15A, 15B:
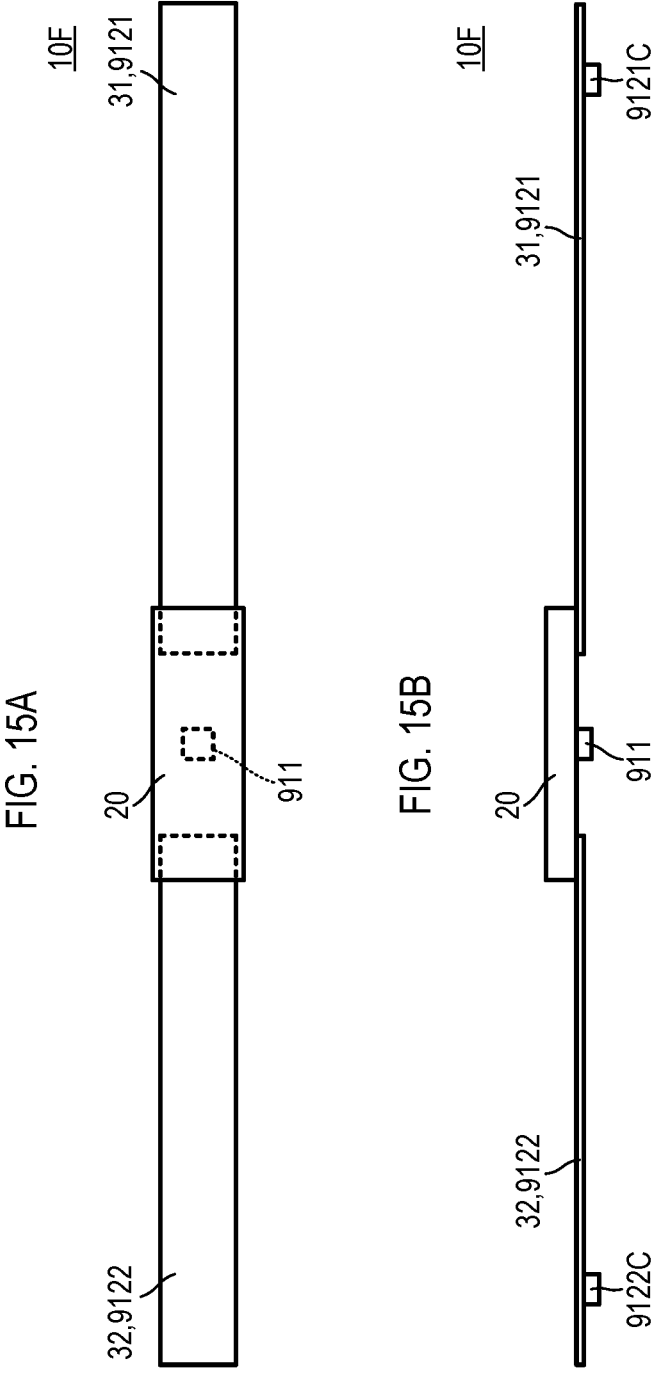
FIG. 15(A) is a plan view of a biological activity detection sensor according to a seventh exemplary embodiment.
FIG. 15(B) is a side view of the biological activity detection sensor according to the seventh exemplary embodiment.

A biological activity detection sensor according to a seventh exemplary embodiment will be described with reference to the drawings. FIG. 15(A) is a plan view of a biological activity detection sensor according to a seventh exemplary embodiment, and FIG. 15(B) is a side view of the biological activity detection sensor according to the seventh exemplary embodiment.

As illustrated in FIGS. 15(A) and 15(B), a biological activity detection sensor 10F according to the seventh embodiment is different from the biological activity detection sensor 10 according to the first embodiment in that a first member 32, a tremor sensor 9121C, and a tremor sensor 9122C are added. Other configurations of the biological activity detection sensor 10F are similar to those of the biological activity detection sensor 10, and description of similar parts is omitted.

In this exemplary aspect, the first member 32 has the same configuration as a first member 31 and functions as the tremor sensor 9122. Moreover, the first member 32 is connected to an end of the second member 20 opposite to an end to which the first member 31 is connected.

The tremor sensor 9121C and the tremor sensor 9122C are chip components according to the exemplary aspect. The tremor sensor 9121C is mounted on the first member 31 and the tremor sensor 9122C is mounted on the first member 32.

With this configuration, the biological activity detection sensor 10F exhibits the same operation and effect as the biological activity detection sensor 10. Moreover, with this configuration, the biological activity detection sensor 10F can detect more tremors. As a result, the biological activity detection sensor 10F can generate biological activity detection information with higher accuracy.

Eighth Exemplary Embodiment

A biological activity detection sensor according to an eighth exemplary embodiment will be described with reference to the drawings. FIG. 16(A) is a side view of a biological activity detection sensor according to an eighth exemplary embodiment, and FIG. 16(B) is an exploded side view of the biological activity detection sensor according to the eighth exemplary embodiment.

As illustrated in FIGS. 16(A) and 16(B), a biological activity detection sensor 10G according to the eighth embodiment is different from the biological activity detection sensor 10A according to the second embodiment in a connection structure of a second member 20, a first member 31, and a first member 32. Other configurations of the biological activity detection sensor 10G are similar to those of the biological activity detection sensor 10A, and description of similar parts is omitted.

The biological activity detection sensor 10G includes the second member 20, the first member 31, the first member 32, a first housing 51, and a second housing 52.

The first housing 51 has a box shape with one surface opened. The second member 20 is accommodated in the first housing 51. At this time, the second member 20 is disposed in the first housing 51 such that a surface on which a motion detection sensor 911 is mounted is exposed to a side of the opening surface.

The second housing 52 has a box shape with one surface opened. The second housing 52 is disposed with respect to the first housing 51 such that the opening surface side of the second housing 52 and the opening surface side of the first housing 51 face each other. The second housing 52 and the first housing 51 are fitted to each other, whereby the second housing 52 is fixed to the first housing 51.

Recesses through which the first member 31 and the first member 32 can be inserted are formed in side walls of the first housing 51 and the second housing 52, respectively. These recesses face each other and overlap each other to form an insertion hole.

The first member 31 and the first member 32 are disposed such that an intermediate position in a longitudinal direction passes through the insertion hole. As a result, longitudinal ends of the first member 31 and the first member 32 are disposed in a space surrounded by the first housing 51 and the second housing 52 through these recesses. In this state, the first member 31 and the first member 32 abut on a surface of the second member 20 on which the motion detection sensor 911 is mounted.

By matching the shapes of the insertion holes with the shapes of the first member 31 and the first member 32, the first housing 51 and the second housing 52 can sandwich and fix the first member 31 and the first member 32. Therefore, the contact state between the first member 31 and the second member 20 and the contact state between the first member 32 and the second member are maintained.

With this configuration, the biological activity detection sensor 10G achieves the same effects as those of the biological activity detection sensor 10A. Moreover, with this configuration, the biological activity detection sensor 10G can maintain the connection state between the second member 20, and the first member 31 and the first member 32 only by fitting the first housing 51 and the second housing 52 without using a conductive bonding material 290 or the like. Note that, at this time, as illustrated in FIGS. 16(A) and 16(B), a cushioning material can be disposed between the second member 20 and the first housing 51 on an opposite side of a mounting surface of the motion detection sensor 911. By disposing the second member 20 so as to be pushed further toward the second housing 52, connection reliability between the second member 20, and the first member 31 and the first member 32 can be improved. Note that, in this configuration, the package component 40 as in the third embodiment may be further provided. In this case, a hole is provided in the first housing 51 so that a connector member is exposed.

Note that, in the embodiment using the connector member 931 described above, a reinforcing layer and a reinforcing member can be added to a mounting location of the connector member 931 in the second member 20. As a result, the reliability of the biological activity detection sensor is improved.

Ninth Exemplary Embodiment

A biological activity detection sensor according to a ninth exemplary embodiment of the present invention will be described with reference to the drawings. FIGS. 17(A), 17(B), 17(C), and 17(D) are side views of a biological activity detection sensor according to a ninth exemplary embodiment.

As illustrated in FIGS. 17(A), 17(B), 17(C), and 17(D), biological activity detection sensors 10HA, 10HB, 10HC, and 10HD according to the ninth embodiment are different from the biological activity detection sensor 10G according to the eighth embodiment in a positional relationship between a tremor sensor 912 and a motion detection sensor 911 and a structure corresponding thereto. Other basic configurations of the biological activity detection sensors 10HA, 10HB, 10HC, and 10HD are similar to those of the biological activity detection sensor 10G, and description of similar parts is omitted.

Figure 17A:
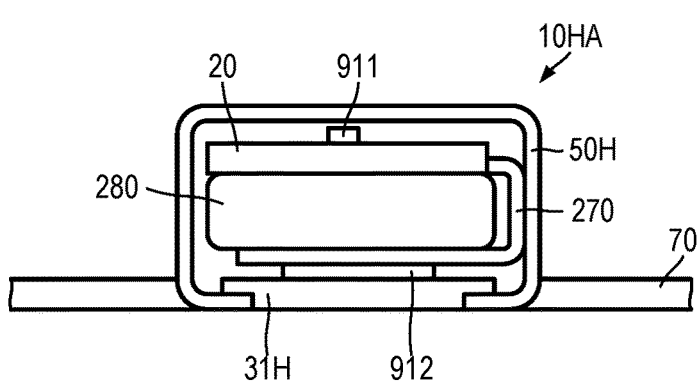
FIGS. 17(A), 17(B), 17(C), and 17(D) are side views of a biological activity detection sensor according to a ninth exemplary embodiment.

As illustrated in FIG. 17(A), the biological activity detection sensor 10HA includes a second member 20, a first member 31H, a housing 50H, a wiring member 270, a battery 280, the motion detection sensor 911, and the tremor sensor 912.

The motion detection sensor 911 is mounted on the second member 20. In plan view of the biological activity detection sensor 10HA, the tremor sensor 912 is disposed at a position overlapping the second member 20.

As further shown, the battery 280 is disposed between the second member 20 and the tremor sensor 912.

The wiring member 270 is disposed substantially along an outer periphery of the battery 280, and electrically connects the tremor sensor 912 and the second member 20. The wiring member 270 can be, for example, a flexible substrate, but it is not limited thereto. For example, the wiring member 270 may have the same degree of rigidity as the second member 20.

The first member 31H is disposed on a surface of the tremor sensor 912 on a side opposite to a side of the second member 20. In other words, the tremor sensor 912 is disposed in the first member 31H.

Moreover, the housing 50H incorporates the second member 20, the first member 31H, the wiring member 270, the battery 280, the motion detection sensor 911, and the tremor sensor 912 except for a surface of the first member 31H opposite to the surface on which the tremor sensor 912 is disposed.

The housing 50H is fixed to a mounting member 70. At this time, the mounting member 70 is attached to the housing 50H such that a region overlapping the tremor sensor 912 in plan view is exposed to the outside on the surface of the first member 31H opposite to the surface on which the tremor sensor 912 is disposed.

The first member 31H can be, for example, insulating rubber that is more easily deformed than the second member 20. In other words, the first member 31H has a lower rigidity than the second member 20.

In such a configuration, the biological activity detection sensor 10HA is mounted on a target site of a subject such that the exposed surface of the first member 31H abuts on the target site.

With this configuration, the biological activity detection sensor 10HA can achieve the same operation and effect as the biological activity detection sensor 10G. Moreover, with this configuration, the biological activity detection sensor 10HA has a small shape in plan view.

Figure 17B:
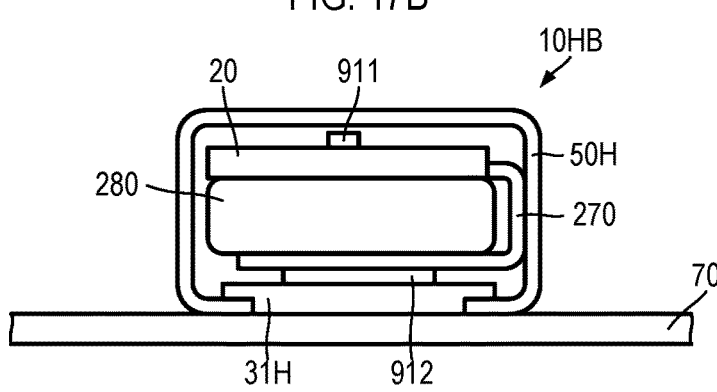

As illustrated in FIG. 17(B), the biological activity detection sensor 10HB is different from the biological activity detection sensor 10HA illustrated in FIG. 17(A) in a fixing aspect to the mounting member 70. Other configurations of the biological activity detection sensor 10HB are the same as those of the biological activity detection sensor 10HA, and the description of the same parts will be omitted.

In the biological activity detection sensor 10HB, the mounting member 70 is disposed on the surface of the housing 50H on the exposed surface side of the first member 31H, and the housing 50H is fixed to the mounting member 70.

With such a configuration, the biological activity detection sensor 10HB exhibits the same operation and effect as the biological activity detection sensor 10HA.

Figure 17C:
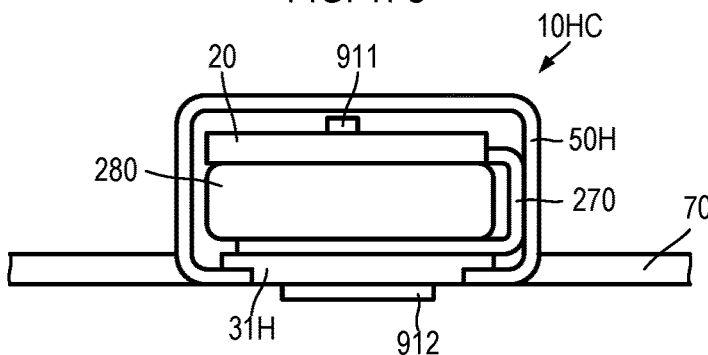

As illustrated in FIG. 17(C), the biological activity detection sensor 10HC differs from the biological activity detection sensor 10HA illustrated in FIG. 17(A) in a positional relationship between a tremor sensor 912 and a first member 31H. Other configurations of the biological activity detection sensor 10HC are similar to those of the biological activity detection sensor 10HA, and description of similar parts is omitted.

The tremor sensor 912 is disposed on a surface of the first member 31H exposed to the outside from a housing 50H. In other words, in a thickness direction of the biological activity detection sensor 10HC, a wiring member 270, the first member 31H, and the tremor sensor 912 are disposed in this order. Although not illustrated, the tremor sensor 912 and the wiring member 270 are electrically connected by a conductor pattern formed on the first member 31H.

With such a configuration, the biological activity detection sensor 10HC exhibits the same operation and effect as the biological activity detection sensor 10HA.

Figure 17D:
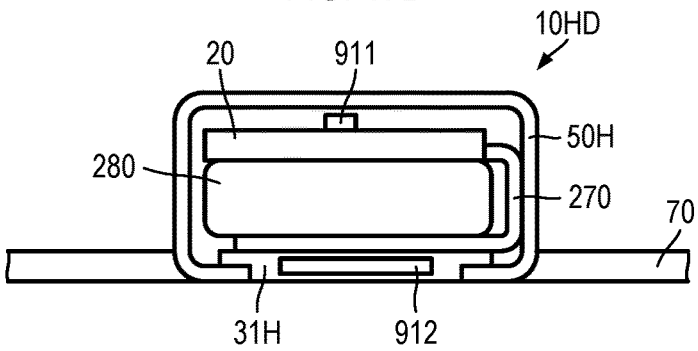

As illustrated in FIG. 17(D), the biological activity detection sensor 10HD differs from the biological activity detection sensor 10HA illustrated in FIG. 17(A) in a positional relationship between a tremor sensor 912 and a first member 31H. Other configurations of the biological activity detection sensor 10HD are similar to those of the biological activity detection sensor 10HA, and description of similar parts is omitted.

The tremor sensor 912 is disposed inside the first member 31H. Although not illustrated, the tremor sensor 912 and the wiring member 270 are electrically connected by a conductor pattern formed on the first member 31H.

With such a configuration, the biological activity detection sensor 10HD can achieve the same action and effect as the biological activity detection sensor 10HA.

Tenth Exemplary Embodiment

Figures 18A, 18B:
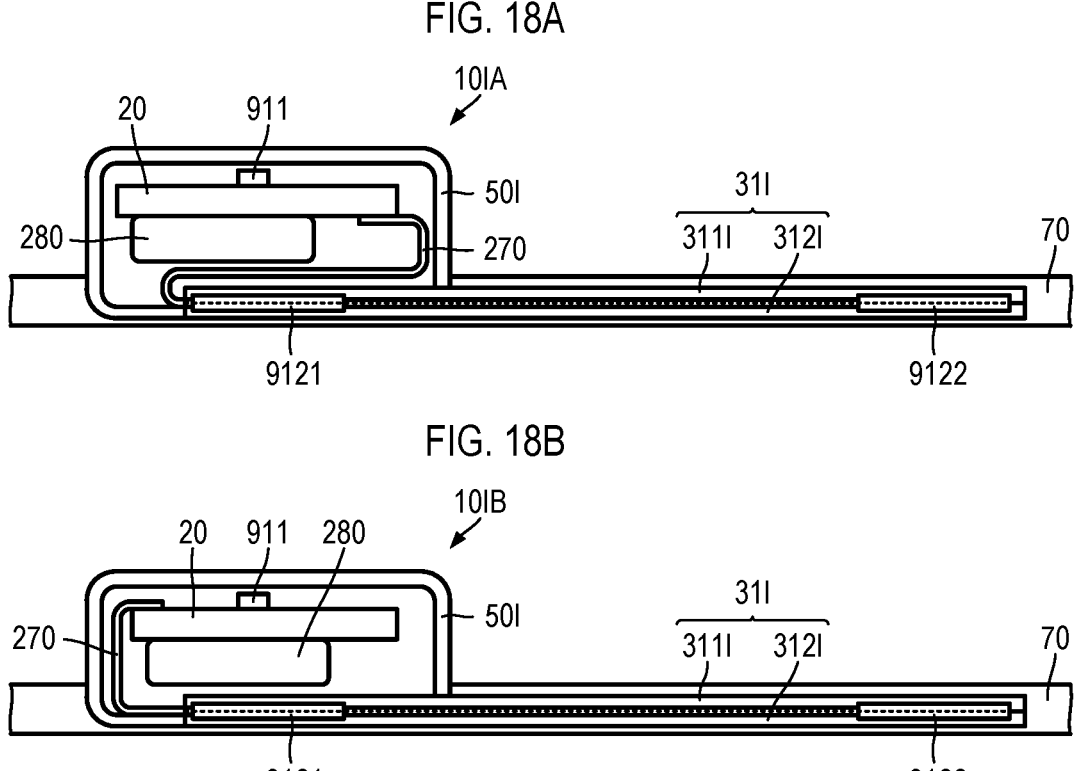
FIGS. 18(A) and 18(B) are side views of a biological activity detection sensor according to a tenth exemplary embodiment.

A biological activity detection sensor according to a tenth exemplary embodiment will be described with reference to the drawings. FIGS. 18(A) and 18(B) are side views of a biological activity detection sensor according to a tenth exemplary embodiment.

As illustrated in FIGS. 18(A) and 18(B), biological activity detection sensors 10IA and 10IB according to the tenth embodiment are different from the biological activity detection sensor 10G according to the eighth embodiment in a positional relationship between a plurality of tremor sensors 9121 and 9122 and a motion detection sensor 911, and a structure corresponding thereto. Other basic configurations of the biological activity detection sensors 10IA and 10IB are similar to those of the biological activity detection sensor 10G, and description of similar parts is omitted.

As illustrated in FIG. 18(A), a biological activity detection sensor 10IA includes a second member 20, a first member 31I, a housing 50I, a wiring member 270, a battery 280, the motion detection sensor 911, and the plurality of tremor sensors 9121 and 9122.

The motion detection sensor 911 is mounted on the second member 20. The first tremor sensor 9121 is disposed at a position overlapping the second member 20 in plan view of the biological activity detection sensor 10IA. The second tremor sensor 9122 is disposed at a position not overlapping the second member 20 in plan view of the biological activity detection sensor 10IA. That is, the first tremor sensor 9121 and the second tremor sensor 9122 are disposed apart from each other at a predetermined distance.

As further shown, the battery 280 is disposed between the second member 20 and the first tremor sensor 9121.

The wiring member 270 electrically connects the second member 20 and the plurality of tremor sensors 9121 and 9122. In an exemplary aspect, the wiring member 270 can be, for example, a flexible substrate, but it is not limited thereto. Furthermore, a part of the wiring member 270 connecting the second member 20 and the first tremor sensor 9121 may be different from a part of the wiring member connecting the first tremor sensor 9122 and the second tremor sensor 9121.

In addition, the first member 31I has an elongated shape extending in a direction in which the plurality of tremor sensors 9121 and 9122 are arranged. The first member 31I includes an insulating resin 311I and an insulating resin 312I. The insulating resin 311I and the insulating resin 312I can be, for example, a silicon resin in an exemplary aspect. Moreover, the insulating resin 311I and the insulating resin 312I are stacked, and the first member 31I is formed by this stacked structure.

The plurality of tremor sensors 9121 and 9122 and the part of the wiring member 270 connecting the plurality of tremor sensors 9121 and 9122 are sandwiched between the insulating resin 311I and the insulating resin 312I.

Moreover, a housing 50I has a box shape incorporating the second member 20, a part of the wiring member 270 connecting the second member 20 and the first tremor sensor 9121, the battery 280, and the motion detection sensor 911.

The first member 31I is fixed to the housing 50I such that a part of the first member 31I where the first tremor sensor 9121 is disposed overlaps the housing 50I and a part of the first member 31I where the second tremor sensor 9122 is disposed does not overlap the housing 50I.

The biological activity detection sensor 10IB is fixed to a mounting member 70 such that first member 31I is incorporated in the mounting member 70.

With this configuration, the biological activity detection sensor 10IA can achieve the same effects as those of the biological activity detection sensor 10G. Moreover, with this configuration, the biological activity detection sensor 10IA can have a small shape in plan view even in a configuration including the plurality of tremor sensors 9121 and 9122.

As illustrated in FIG. 18(B), the biological activity detection sensor 10IB differs from the biological activity detection sensor 10IA illustrated in FIG. 18(A) only in a connection aspect between a second member 20 and a first tremor sensor 9121 by a wiring member 270, and thus detailed description is omitted. With this configuration, the biological activity detection sensor 10IB can achieve the same operation and effect as the biological activity detection sensor 10IA.

Furthermore, the configurations of the above-described embodiments can be appropriately combined, and functions and effects according to the respective combinations can be exhibited.

REFERENCE SIGNS LIST 10, 10A, 10B, 10C, 10D, 10E, 10F, 10G, 10HA, 10HB, 10HC, 10HD, 10IA, 10IB biological activity detection sensor
20, 20D second member
21, 22 rigid part
23 flexible part
29 first member insertion fitting member
31, 31C, 32, 31H, 31I first member
40 package component
41 circuit board
50H, 50I housing
51 first housing
52 second housing
60 insulating protective layer
70 mounting member
70A mounting member
71, 72 pocket
80 ankle
91, 91A sensor
92 circuit module
200 flexible layer
270 wiring member
280 battery
290 conductive bonding material
400 housing
911 motion detection sensor
912, 912C, 9121, 9121C, 9122, 9122C tremor sensor
920 power supply
921 arithmetic operation unit
922 signal processing unit
923 communication unit
924 storage unit
930 connector
931, 932 connector member

What is claimed:

1. A biological activity detection sensor comprising:
a motion detection sensor configured to detect a motion of a living body;
a tremor sensor configured to detect a tremor of the living body;
a base member that includes:
a first member comprising a first material that is deformable in accordance with a mounted state on the living body, and
a second member comprising a second material that is less deformable than the first member; and
an insulating protective layer having a lower rigidity than the second member,
wherein the tremor sensor is provided in the first member, and the motion detection sensor is in the second member, wherein the tremor sensor and the first member are separate components from one another, and wherein, at least in a region where the first member does not overlap the second member, the insulating protective layer covers the first member and the tremor sensor such that the first member and the tremor sensor are enclosed therein.

2. The biological activity detection sensor according to claim 1, wherein the tremor sensor is mounted on the first member.

3. The biological activity detection sensor according to claim 1, wherein:

the tremor sensor is configured using the first member, the first material forming the first member is configured to generate a voltage or a current in response to a displacement thereof, and the tremor sensor is configured to detect the tremor based on the generated voltage or the generated current that corresponds to the displacement.

4. The biological activity detection sensor according to claim 1, wherein the insulating protective layer covers at least a part of the first member and the second member and comprises a material that is more deformable than the second material of the second member.

5. The biological activity detection sensor according to claim 1, further comprising a circuit module configured to process a tremor detection signal provided by the tremor sensor and a motion detection signal provided by the motion detection sensor to generate biological activity detection information.

6. The biological activity detection sensor according to claim 5, wherein the second member comprises the circuit module.

7. The biological activity detection sensor according to claim 5, wherein the circuit module is separate from the first member and the second member and is detachably connected to the second member.

8. The biological activity detection sensor according to claim 7, further comprising:

a package component that forms the circuit module, wherein the second member includes a connector member connected to the package component, and wherein the connector member and the motion detection sensor are disposed at positions where the connector member and the motion detection sensor do not overlap each other in a plan view of the second member.

9. The biological activity detection sensor according to claim 5, wherein:

a first part of the circuit module is separate from the first member and the second member, and the second member includes a second part of the circuit module, and the first part of the circuit module is detachably connected to the second member.

10. The biological activity detection sensor according to claim 1, wherein the first member comprises two first members that each have a shape extending in a longitudinal direction, wherein one end in the longitudinal direction of one of the two first members is connected to one end of the second member, and one end in the longitudinal direction of another of the two first members is connected to another end of the second member.

11. The biological activity detection sensor according to claim 1, further comprising a conductive bonding material that directly connects the first member to the second member.

12. The biological activity detection sensor according to claim 1, wherein:

the second member includes a first member insertion fitting member having a recess, and the first member is configured to be inserted into the first member insertion fitting member to connect to the second member.

13. The biological activity detection sensor according to claim 1, wherein:

the second member is a stacked body having a plurality of stacked layers, and a part of the first member forms a part of the plurality of stacked layers.

14. The biological activity detection sensor according to claim 1, further comprising:

a first housing configured to accommodate the second member; and a second housing fitted to the first housing, wherein the first member is connected and fixed to the second member by fitting the first housing and the second housing.

15. The biological activity detection sensor according to claim 1, wherein the second member includes a plurality of rigid parts and at least one flexible part that connects the plurality of rigid parts.

16. The biological activity detection sensor according to claim 1, further comprising a mounting member including a housing part that houses at least the first member, with the mounting member being in contact with the living body.

17. The biological activity detection sensor according to claim 1, wherein the first material of the first member has a Young's modulus lower than the second material of the second member.

18. The biological activity detection sensor according to claim 1, wherein the first member is electrically and physically connected to the second member.

19. A biological activity detection sensor comprising:

a motion detection sensor configured to detect a motion of a living body;

a tremor sensor configured to detect a tremor of the living body;

a base member that includes:

a first member with the tremor sensor provided in the first member, and a second member with the motion detection sensor provided in the second member; and an insulating protective layer having a lower rigidity than the second member, wherein the tremor sensor and the first member are separate components from one another, wherein the second member is formed of a material that is less deformable than a material of the first member, and wherein, at least in a region where the first member does not overlap the second member, the insulating protective layer covers the first member and the tremor sensor such that the first member and the tremor sensor are enclosed therein.

20. The biological activity detection sensor according to claim 19, wherein:

the tremor sensor is configured using the first member, the first material forming the first member is configured to generate a voltage or a current in response to a displacement thereof, and the tremor sensor is configured to detect the tremor of the living body based on the generated voltage or the generated current that corresponds to the displacement.

\* \* \* \* \*